US012390279B1

(12) United States Patent
Zhu et al.

(10) Patent No.: US 12,390,279 B1
(45) Date of Patent: Aug. 19, 2025

(54) METHOD AND SYSTEM FOR SIMULATING TEMPOROMANDIBULAR JOINT (TMJ) SURGERY BASED ON ARTIFICIAL INTELLIGENCE (AI) TECHNOLOGY

(71) Applicant: Sichuan University, Chengdu (CN)

(72) Inventors: Songsong Zhu, Chengdu (CN); Ruiye Bi, Chengdu (CN); Han Fang, Chengdu (CN); Yanjing Zhan, Chengdu (CN); Yao Liu, Chengdu (CN); Nan Jiang, Chengdu (CN); Peng Wang, Chengdu (CN); Haopeng Yu, Chengdu (CN); Xianni Yang, Chengdu (CN); Haohan Li, Chengdu (CN)

(73) Assignee: Sichuan University, Chengdu (CN)

( * ) Notice: Subject to any disclaimer, the term of this patent is extended or adjusted under 35 U.S.C. 154(b) by 0 days.

(21) Appl. No.: 19/176,358

(22) Filed: Apr. 11, 2025

(30) Foreign Application Priority Data

Sep. 9, 2024 (CN) .......................... 202411253738.9

(51) Int. Cl.
- *A61B 34/10* (2016.01)
- *A61B 17/56* (2006.01)
- *G06T 7/00* (2017.01)

(52) U.S. Cl.
CPC .............. *A61B 34/10* (2016.02); *A61B 17/56* (2013.01); *G06T 7/0012* (2013.01); *A61B 2017/564* (2013.01); *A61B 2034/105* (2016.02); *G06T 2207/10004* (2013.01); *G06T 2207/20112* (2013.01); *G06T 2207/30008* (2013.01)

(58) Field of Classification Search
None
See application file for complete search history.

(56) References Cited

U.S. PATENT DOCUMENTS

2023/0320823 A1* 10/2023 Marshall .............. A61C 19/045
433/69

OTHER PUBLICATIONS

Villamil, Marta B., et al. "Simulation of the human TMJ behavior based on interdependent joints topology." Computer methods and programs in biomedicine 105.3 (2012): 217-232. (Year: 2012).*

(Continued)

*Primary Examiner* — Samah A Beg
(74) *Attorney, Agent, or Firm* — Bayramoglu Law Offices LLC

(57) ABSTRACT

A method for simulating temporomandibular joint (TMJ) surgery based on an artificial intelligence (AI) technology includes: obtaining temporal bone corners and a temporal bone edge contour in each TMJ image based on a motion synchronization degree of and a distance between any two corners in each TMJ image; obtaining a plurality of mandible corners and a mandible motion direction based on a distance between the temporal bone corners in each TMJ image and coordinates of the corners in the TMJ image in a coordinate system; obtaining a real mandible edge contour in each TMJ image based on an edge contour on which the mandible corners are located and the mandible motion direction in each TMJ image; and constructing a TMJ anatomical model based on the real mandible edge contours and the temporal bone edge contours in all TMJ images.

2 Claims, 2 Drawing Sheets

(56) References Cited

OTHER PUBLICATIONS

Celebi, Nukhet, et al. "Development of a mandibular motion simulator for total joint replacement." Journal of Oral and Maxillofacial Surgery 69.1 (2011): 66-79. (Year: 2011).*
Al-Saleh, Mohammed AQ, et al. "Three-dimensional assessment of temporomandibular joint using MRI-CBCT image registration." PLoS One 12.1 (2017): e0169555. (Year: 2017).*

* cited by examiner

METHOD AND SYSTEM FOR SIMULATING TEMPOROMANDIBULAR JOINT (TMJ) SURGERY BASED ON ARTIFICIAL INTELLIGENCE (AI) TECHNOLOGY

CROSS REFERENCE TO THE RELATED APPLICATIONS

This application is based upon and claims priority to Chinese Patent Application No. 202411253738.9, filed on Sep. 9, 2024, the entire contents of which are incorporated herein by reference.

TECHNICAL FIELD

The present disclosure relates to the field of healthcare informatics, and specifically, to a method and system for simulating temporomandibular joint (TMJ) surgery based on an artificial intelligence (AI) technology.

BACKGROUND

At present, a system for simulating TMJ surgery based on AI is established in hospitals such that doctors can perform simulation exercises before real surgery and discover potential risks in the surgery in advance. An anatomical model of a TMJ when a patient opens and closes the mouth needs to be determined before TMJ surgery. Generally, the anatomical model may be established by determining a position relationship between a temporal bone and a mandible during mouth opening and closing through a magnetic resonance imaging (MRI) video of the patient. When the position relationship between the temporal bone and the mandible during mouth opening and closing is determined, the TMJ is affected by activities such as chewing and opening the mouth. In MRI, artifacts appear in some video images due to motion blur. When a distance between TMJs is determined through edge detection, there are a plurality of edges of the mandible and a real edge of the mandible cannot be recognized. This reduces accuracy of simulating TMJ surgery.

SUMMARY

The present disclosure provides a method and system for simulating TMJ surgery based on an AI technology, to resolve a problem in the prior art that there are a plurality of edges of a mandible and a real edge of the mandible cannot be recognized when a distance between TMJs is determined through edge detection.

The method and system for simulating TMJ surgery based on an AI technology according to the present disclosure adopt the following technical solutions:

An embodiment of the present disclosure provides a method for simulating TMJ surgery based on an AI technology. The method includes the following steps:

obtaining a plurality of TMJ images and corners corresponding to each corner in each TMJ image in other TMJ images;

constructing a coordinate system of each TMJ image; in the coordinate system, obtaining a motion synchronization degree of any two corners in each TMJ image based on a distance between coordinates of each of the any two corners in the TMJ image and coordinates of the corresponding corner in the adjacent TMJ image; and obtaining temporal bone corners and a temporal bone edge contour in each TMJ image based on the motion synchronization degree of and a distance between the any two corners in each TMJ image;

obtaining a plurality of mandible corners and a mandible motion direction based on a distance between the temporal bone corners in each TMJ image and coordinates of the corners in the TMJ image in the coordinate system;

obtaining a real mandible edge contour in each TMJ image based on an edge contour on which the mandible corners are located and the mandible motion direction in each TMJ image; and constructing a TMJ anatomical model based on the real mandible edge contours and the temporal bone edge contours in all TMJ images.

Preferably, the obtaining a motion synchronization degree of any two corners in each TMJ image based on a distance between coordinates of each of the any two corners in the TMJ image and coordinates of the corresponding corner in the adjacent TMJ image is specifically implemented based on the following formula:

$$B_{u,v} = \frac{1}{n-1} \sum_{i=1}^{n-1} \left( \frac{|C_{u,i} - C_{v,i}|}{C_{u,i} \times C_{v,i}} \right)$$

where $B_{u,v}$ represents a motion synchronization degree of the $u^{th}$ corner and the $v^{th}$ corner in each TMJ image; n represents a quantity of the TMJ images; $C_{u,i}$ represents a distance between the coordinates of the $u^{th}$ corner in the $i^{th}$ TMJ image and the coordinates of the corresponding corner in the $(i+1)^{th}$ TMJ image in the coordinate system; $C_{v,i}$ represents a distance between the coordinates of the $v^{th}$ corner in the $i^{th}$ TMJ image and the coordinates of the corresponding corner in the $(i+1)^{th}$ TMJ image in the coordinate system; and | | represents an absolute value function.

Preferably, the obtaining temporal bone corners and a temporal bone edge contour in each TMJ image based on the motion synchronization degree of and a distance between the any two corners in each TMJ image specifically includes the following steps:

obtaining a motion synchronization index between the any two corners in each TMJ image based on the motion synchronization degree of and the distance between the any two corners in each TMJ image; and obtaining the temporal bone corners and the temporal bone edge contour in each TMJ image based on the motion synchronization index between the any two corners in each TMJ image.

Preferably, the obtaining a motion synchronization index between the any two corners in each TMJ image based on the motion synchronization degree of and the distance between the any two corners in each TMJ image is specifically implemented based on the following formula:

$$E_{u,v} = B_{u,v} \times \frac{1}{n} \sum_{i=1}^{n} |L_{i,u,v} - \overline{L}|$$

where $E_{u,v}$ represents a motion synchronization index between the $u^{th}$ corner and the $v^{th}$ corner in each TMJ image; $B_{u,v}$ represents the motion synchronization degree of the $u^{th}$ corner and the $v^{th}$ corner in each TMJ image; n represents a quantity of the TMJ images; $L_{i,u,v}$ represents an Euclidean distance between the $u^{th}$ corner and the $v^{th}$ corner in the $i^{th}$ TMJ image; $\overline{L}$ represents an average Euclidean distance between the $u^{th}$ corner and the $v^{th}$ corner in all TMJ images; and | | represents the absolute value function.

Preferably, the obtaining the temporal bone corners and the temporal bone edge contour in each TMJ image based on the motion synchronization index between the any two corners in each TMJ image specifically includes the following step:

in each TMJ image, recording the two corners corresponding to a minimum motion synchronization index as the temporal bone corners, and an edge contour on which the temporal bone corners are located as the temporal bone edge contour.

Preferably, the obtaining a plurality of mandible corners and a mandible motion direction based on a distance between the temporal bone corners in each TMJ image and coordinates of the corners in the TMJ image in the coordinate system specifically includes the following steps:

in each TMJ image, recording a center point of a line segment connecting the two temporal bone corners as a reference point, performing clockwise rotation from a horizontal right direction to a horizontal left direction to construct a semicircle with the reference point as a circle center and y times a distance between the two temporal bone corners as a radius, and recording the corners in the semicircle which are not temporal bone corners as suspected mandible corners, where n y represents a preset coefficient;

in the coordinate system, forming a vector of the $z^{th}$ suspected mandible corner in the $i^{th}$ TMJ image based on a distance and a direction from the coordinates of the $z^{th}$ suspected mandible corner in the $i^{th}$ TMJ image to the coordinates of the corresponding corner in the $(i+t)^{th}$ TMJ image;

performing anomaly detection on all suspected mandible corners through a local outlier factor (LOF) algorithm based on a direction of the vector of each suspected mandible corner in the $i^{th}$ TMJ image, to obtain abnormal mandible corners; and recording all suspected mandible corners except the abnormal mandible corners as the mandible corners; and recording a direction of a sum vector of the vectors of all mandible corners in the $i^{th}$ TMJ image as the mandible motion direction in the $i^{th}$ TMJ image.

Preferably, the obtaining a real mandible edge contour in each TMJ image based on an edge contour on which the mandible corners are located and the mandible motion direction in each TMJ image specifically includes the following steps:

obtaining a similar mandibular edge index of each TMJ image based on the edge contour on which the mandible corners are located and the mandible motion direction in each TMJ image; and obtaining the real mandible edge contour in each TMJ image based on the similar mandibular edge index of each TMJ image.

Preferably, the obtaining a similar mandibular edge index of each TMJ image based on the edge contour on which the mandible corners are located and the mandible motion direction in each TMJ image specifically includes the following steps:

recording the edge contour on which the mandible corners are located in each TMJ image as a mandible edge contour;

obtaining a vector of a center of a minimum circumcircle of each mandible edge contour in each TMJ image in a manner of obtaining the vector of the $z^{th}$ suspected mandible corner in the $i^{th}$ TMJ image;

in each TMJ image, recording the vector of the center of the minimum circumcircle of each mandible edge contour as a motion vector of each mandible edge contour;

recording the $i^{th}$ to $(i+t)^{th}$ TMJ images as reference TMJ images corresponding to the $i^{th}$ TJM image;

recording a direction of a sum vector of the motion vectors of all mandible edge contours in all reference TMJ images as a mandible edge contour motion direction corresponding to the $i^{th}$ TMJ image; and calculating the similar mandibular edge index of the $i^{th}$ TMJ image based on the following formula:

$$P_i = \theta'_i \times \sum_{s=2}^{M} |a_s - a_{s-1}|$$

where $P_i$ represents the similar mandibular edge index of the $i^{th}$ TMJ image; $\theta'_i$ represents a minimum included angle between the mandible motion direction and the mandible edge contour motion direction corresponding to the $i^{th}$ TMJ image; $a_s$ represents an average curvature of all mandible edge contours in the $s^{th}$ reference TMJ image; $a_{s-1}$ represents an average curvature of all mandible edge contours in the $(s-1)^{th}$ reference TMJ image; | | represents the absolute value function; and M represents a quantity of the reference TMJ images.

Preferably, the obtaining the real mandible edge contour in each TMJ image based on the similar mandibular edge index of each TMJ image specifically includes the following step:

equally grouping all TMJ images into a plurality of TMJ image sequences, and using the mandible edge contour in the TMJ image corresponding to the smallest similar mandibular edge index in each TMJ image sequence as the real mandible edge contour in each TMJ image.

The present disclosure further provides a system for simulating TMJ surgery based on an AI technology, including a memory, a processor, and a computer program stored in the memory and executable on the processor. The processor executes the computer program stored in the memory to implement the steps of the method for simulating TMJ surgery based on an AI technology.

The technical solutions of the present disclosure have the following beneficial effects: The motion synchronization degree of any two corners in each TMJ image is obtained based on the distance between the coordinates of each of the any two corners in the TMJ image and the coordinates of the corresponding corner in the adjacent TMJ image. The temporal bone corners and the temporal bone edge contour in each TMJ image are obtained based on the motion synchronization degree of and the distance between the any two corners in each TMJ image. The plurality of mandible corners and the mandible motion direction are obtained based on the distance between the temporal bone corners in each TMJ image and the coordinates of the corners in the TMJ image in the coordinate system. The real mandible edge contour in each TMJ image can be accurately obtained, and reliability of a TMJ surgery simulation model is improved. The real mandible edge contour in each TMJ image is obtained based on the edge contour on which the mandible corners are located and the mandible motion direction in each TMJ image. The TMJ anatomical model is constructed based on the real mandible edge contours and the temporal bone edge contours in all TMJ images. A reliable TMJ model can be constructed by obtaining a temporal bone edge and a real mandible edge, to increase reliability of patient treatment and improve a success rate of TMJ surgery.

BRIEF DESCRIPTION OF THE DRAWINGS

To describe the technical solutions in the embodiments of the present disclosure or in the prior art more clearly, the following briefly describes the accompanying drawings required for describing the embodiments or the prior art. Apparently, the accompanying drawings in the following description show merely some embodiments of the present disclosure, and a person of ordinary skill in the art may still derive other drawings from these accompanying drawings without creative efforts.

DETAILED DESCRIPTION OF THE EMBODIMENTS

To further describe the adopted technical means and the effects of the present disclosure to achieve an intended purpose of the disclosure, the following describes specific implementations, structures, features, and effects of a method and system for simulating TMJ surgery based on an AI technology according to the present disclosure in detail with reference to the accompanying drawings and preferred embodiments. In the following description, different references to "an embodiment" or "another embodiment" are not necessarily to the same embodiment. In addition, particular features, structures, or characteristics in one or more embodiments may be combined in any suitable form.

Unless otherwise defined, all technical and scientific terms used herein have the same meanings as commonly understood by those skilled in the technical field of the present disclosure.

Specific solutions of the method and system for simulating TMJ surgery based on an AI technology according to the present disclosure are described below with reference to the accompanying drawings.

Figure 1:
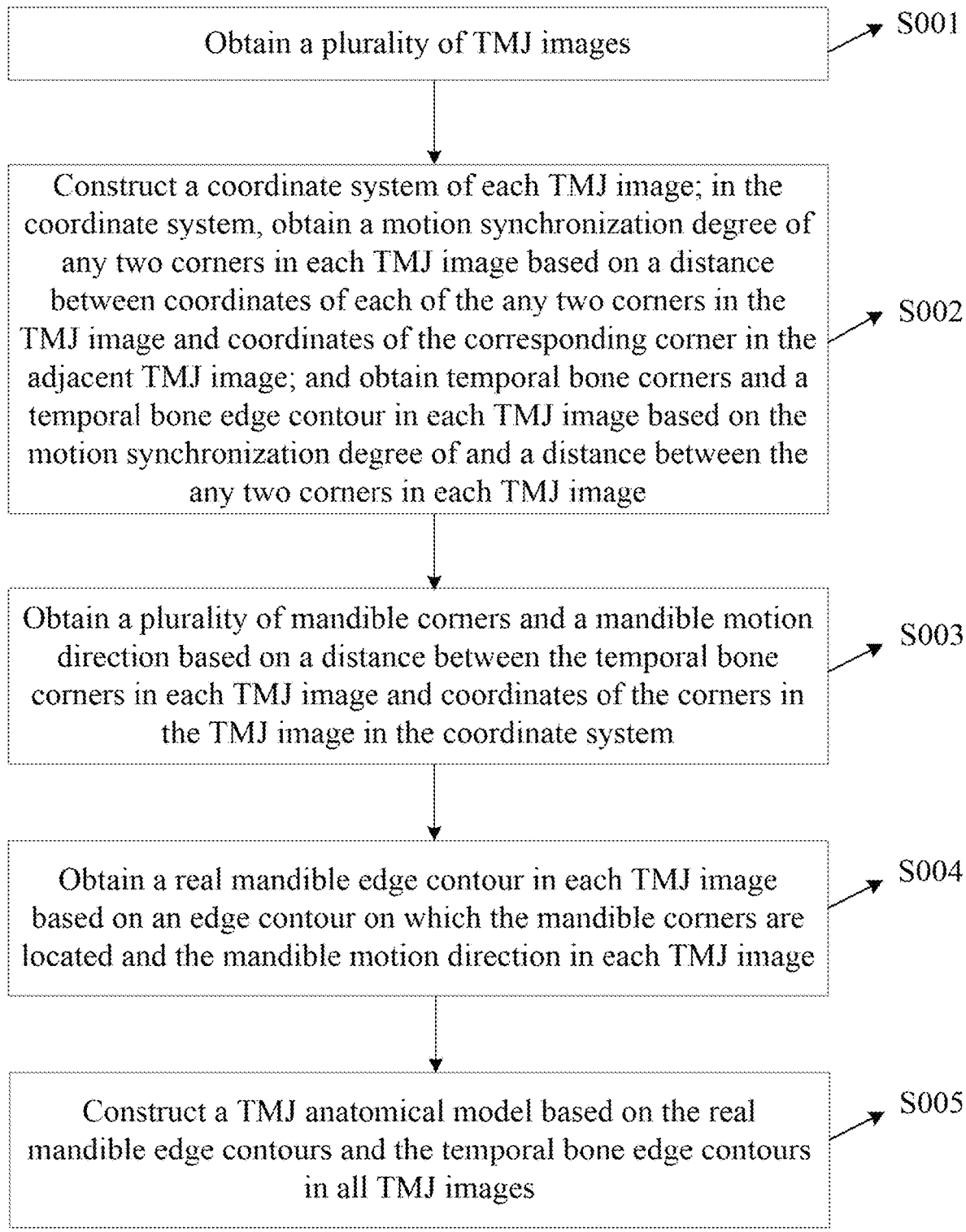
FIG. 1 is a flowchart of a method for simulating TMJ surgery based on an AI technology according to the present disclosure.

FIG. 1 is a flowchart of a method for simulating TMJ surgery based on an AI technology according to an embodiment of the present disclosure. The method includes the following steps:

S001: Obtain a plurality of TMJ images.

It should be noted that a patient needs to undergo an MRI examination before TMJ surgery. During the MRI examination, the patient needs to open and close the mouth to determine the patient's current TMJ condition during mouth opening and closing. An operator may record a video during an MRI scan and use the recorded video to assist in subsequent treatment. All frames of the video are converted to grayscale to obtain the TMJ images.

In this way, the plurality of consecutive TMJ images are obtained.

S002: Construct a coordinate system of each TMJ image; in the coordinate system, obtain a motion synchronization degree of any two corners in each TMJ image based on a distance between coordinates of each of the any two corners in the TMJ image and coordinates of the corresponding corner in the adjacent TMJ image; and obtain temporal bone corners and a temporal bone edge contour in each TMJ image based on the motion synchronization degree of and a distance between the any two corners in each TMJ image.

It should be noted that because a temporal bone and a mandible have projections, they can be recognized through corners as follows: First, determine an edge position of the temporal bone based on a position relationship of the same corner. Then, with the temporal bone as a reference, determine a motion direction of a mandibular joint based on a position relationship of suspected mandible corners in a plurality of frames. Finally, determine a real edge of the mandible based on the motion direction of the mandibular joint and mandibular edge conditions in adjacent frames.

Figure 2:
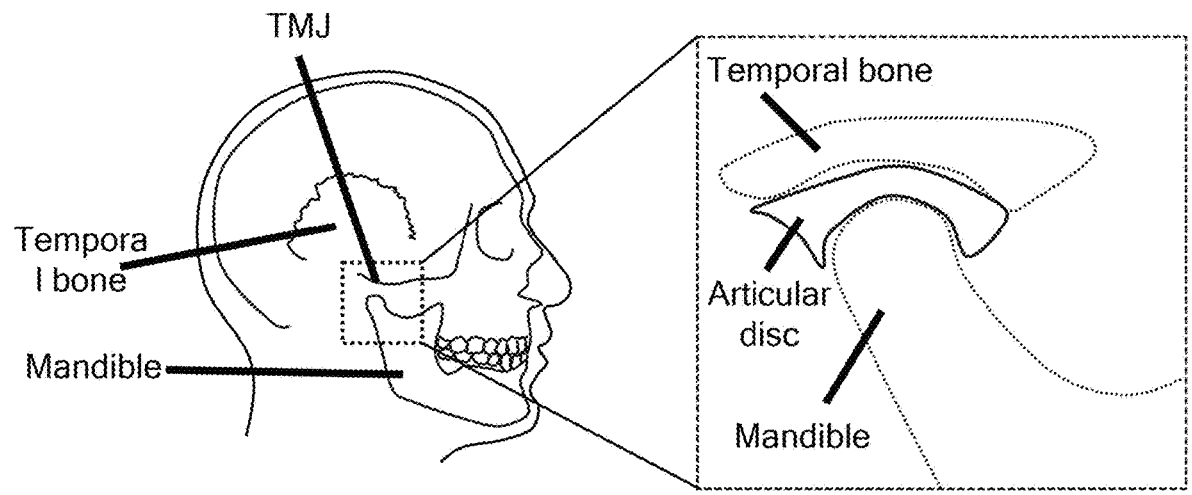
FIG. 2 is a schematic diagram of a TMJ of a human body according to an embodiment.

It should be noted that a TMJ of a human body is schematically shown in FIG. 2. The TMJ is mainly composed of a mandible, a temporal bone, and an articular disc. In an MRI image of the TMJ, an articular fossa of the temporal bone usually appears as a distinctly depressed region, and there are projections on both sides of the temporal bone, namely articular processes. Condyles of the mandible are upward extensions of the mandible that interact with the articular fossa of the temporal bone to allow the mandible to open and close. In the MRI image, the condyles usually appear as rounded projections, and the articular disc is invisible. During mouth opening and closing, when the mouth is closed, the condyles of the mandible slide into the articular fossa of the temporal bone, and the articular disc is located above the condyles to assist in cushioning and reduce friction; and when the mouth is opened, the condyles slide along the articular fossa and gradually move downward, and the articular disc moves forward and rotates with the condyles to adapt to descent and advancement of the mandible. When the TMJ moves, the articular fossa of the temporal bone is adjusted slightly and adaptively to adapt to motion of the mandible.

It should be noted that during mouth opening and closing, a position of the temporal bone moves slightly, whereas the mandible slides with the articular fossa and moves downward. In the TMJ image, the articular processes of the temporal bone locally have obvious grayscale changes.

Harris corner detection is performed on each TMJ image to obtain all corners in each grayscale image of the TMJ video.

Corners in each TMJ image are matched with corners in other TMJ images through optical flow to obtain corners corresponding to each corner in each TMJ image in other TMJ images.

Harris corner detection and optical flow are well-known techniques, and specific methods are not described herein.

Edge detection is performed on each TMJ image to obtain an edge contour.

It should be noted that only the corners on the edge contour are analyzed subsequently in this embodiment.

The coordinate system is constructed with a vertex in an upper left corner of each TMJ image as an origin, a horizontal right direction as a horizontal axis, and a vertically downward direction as a vertical axis.

It should be noted that a pixel of the corner in each image is matched to determine a change distance of the corner at a current position. Because there are corners on both sides of the articular process, any two corners in each grayscale image may be obtained. For all corners determined in each image, because there are corners on both sides of the articular process, any two corners in each image are obtained, and articular process corners of the temporal bone are determined based on a position relationship of the corners.

A motion synchronization degree of the $u^{th}$ corner and the $v^{th}$ corner in each TMJ image is calculated based on the following formula:

$$B_{u,v} = \frac{1}{n-1}\sum_{i=1}^{n-1}\left(\frac{|C_{u,i} - C_{v,i}|}{C_{u,i} \times C_{v,i}}\right)$$

$B_{u,v}$ represents the motion synchronization degree of the $u^{th}$ corner and the $v^{th}$ corner in each TMJ image. n represents a quantity of the TMJ images. $C_{u,i}$ represents a distance between the coordinates of the $u^{th}$ corner in the $i^{th}$ TMJ image and the coordinates of the corresponding corner in the $(i+1)^{th}$ TMJ image in the coordinate system. $C_{v,i}$ represents a distance between the coordinates of the $v^{th}$ corner in the $i^{th}$ TMJ image and the coordinates of the corresponding corner in the $(i+1)^{th}$ TMJ image in the coordinate system. | | represents an absolute value function.

It should be noted that when a denominator in the formula is 0, the denominator is set to 1. This is used as an example for description and to ensure that the formula holds true.

It should be noted that $$\frac{|C_{u,i} - C_{v,i}|}{C_{u,i} \times C_{v,i}}$$

represents that the distances between the coordinates of the corners in the $i^{th}$ TMJ image and the coordinates of the corresponding corners in the (i+1)th TMJ image in the coordinate system are consistent, and the corners move slightly.

At this point, the motion synchronization degree of the any two corners in each TMJ image is obtained.

A motion synchronization index between the $u^{th}$ corner and the $v^{th}$ corner in each TMJ image is calculated based on the following formula:

$$E_{u,v} = B_{u,v} \times \frac{1}{n}\sum_{i=1}^{n}|L_{i,u,v} - \overline{L}|$$

$E_{u,v}$ represents the motion synchronization index between the $u^{th}$ corner and the $v^{th}$ corner in each TMJ image. $B_{u,v}$ represents the motion synchronization degree of the $u^{th}$ corner and the $v^{th}$ corner in each TMJ image. n represents the quantity of the TMJ images. $L_{i,u,v}$ represents an Euclidean distance between the $u^{th}$ corner and the $v^{th}$ corner in the $i^{th}$ TMJ image. L represents an average Euclidean distance between the $u^{th}$ corner and the $v^{th}$ corner in all TMJ images. | | represents the absolute value function.

It should be noted that $L_{i,u,v}$-L represents that a relative distance between the two corners in the TMJ images is constant, and a smaller value indicates that the two corners are corners on both sides of the articular process. When the value of $E_{u,v}$ is smallest, the corners are corners on both sides of the articular process. Because the position of the temporal bone moves slightly during mouth opening and closing, the position of the temporal bone in the joint can be determined after the position of the articular process corners are determined.

In each TMJ image, the two corners corresponding to a minimum motion synchronization index are recorded as the temporal bone corners, and an edge contour on which the temporal bone corners are located is recorded as the temporal bone edge contour.

It should be noted that when there are a plurality of minimum motion synchronization indexes in each TMJ image, any one of them is selected as an example for analysis.

At this point, the two temporal bone corners and the temporal bone edge contour in each TMJ image are obtained.

S003: Obtain a plurality of mandible corners and a mandible motion direction based on a distance between the temporal bone corners in each TMJ image and coordinates of the corners in the TMJ image in the coordinate system.

It should be noted that during mouth opening and closing, the mandible slides along the articular fossa, and the mandible has artifacts in the TMJ image. Consequently, when edge detection is performed on the TMJ image, a plurality of edges may appear, and a real mandible edge cannot be determined. Because the mandible also has recognizable corners, the motion direction of the mandible in adjacent TMJ images can be determined based on changes in the corners.

It should be noted that because the corner of the mandible slides downward and a sliding amplitude may be large, a corner change between adjacent TMJ images can be analyzed to determine a local sliding direction of the mandible in a short period of time. In subsequent model construction, sliding directions in a plurality of short periods of time are integrated to determine a local sliding direction of the mandible in the entire mouth opening and closing process.

It should be noted that because a sliding direction obtained from adjacent TMJ images is too small and may have an error, a plurality of adjacent TMJ images are selected.

A preset quantity threshold t is 4. An example in which each TMJ image and t adjacent TMJ images are selected for analysis is used for description.

It should be noted that because the mandible slides, the position of the temporal bone moves slightly during mouth opening and closing, and this embodiment is mainly intended to determine an edge position relationship between the temporal bone and the mandible, the temporal bone is approximated as a reference point, and the sliding direction of the mandible in the/adjacent TMJ images is determined.

It should be noted that because the condyle of the mandible is located below the articular process of the temporal bone, it can be determined that a condyle edge of the mandible is close to the two corners of the articular process.

It should be noted that positions of the two corners of the temporal bone do not change. Because the condyle of the mandible is located below the articular process of the temporal bone, it can be determined that the condyle edge of the mandible is close to the two corners of the articular process.

A vector between relative positions of the same corner in different TMJ video frames is the motion direction of the mandible. Because there may be corners that do not belong to the mandible, vector differences relative to other corners are large.

In each TMJ image, a center point of a line segment connecting the two temporal bone corners is recorded as a reference point. Clockwise rotation is performed from the horizontal right direction to the horizontal left direction to construct a semicircle with the reference point as a circle center and y times a distance between the two temporal bone corners as a radius. The corners in the semicircle which are not temporal bone corners are recorded as suspected mandible corners. y represents a preset coefficient.

In the coordinate system, a vector of the $z^{th}$ suspected mandible corner in the $i^{th}$ TMJ image is formed based on a distance and a direction from the coordinates of the $z^{th}$ suspected mandible corner in the $i^{th}$ TMJ image to the coordinates of the corresponding corner in the $(i+t)^{th}$ TMJ image.

At this point, the vector of each suspected mandible corner in the $i^{th}$ TMJ image is obtained.

Anomaly detection is performed on all suspected mandible corners through a LOF algorithm based on a direction of the vector of each suspected mandible corner in the $i^{th}$ TMJ image, to obtain abnormal mandible corners. All suspected mandible corners except the abnormal mandible corners are recorded as the mandible corners.

The LOF algorithm is a well-known technique, and a specific method is not described herein.

Figure 3:
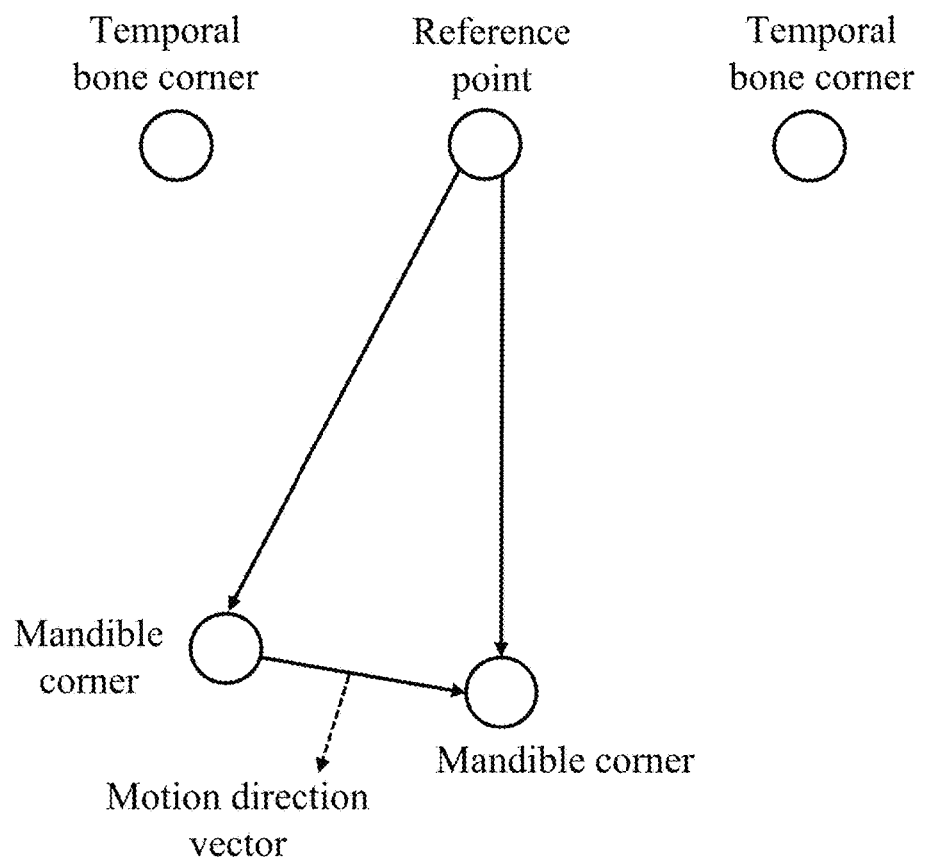
FIG. 3 is a schematic diagram of obtaining a mandible motion direction in each TMJ image according to an embodiment.

A direction of a sum vector of the vectors of all mandible corners in the $i^{th}$ TMJ image is recorded as the mandible motion direction in the $i^{th}$ TMJ image. FIG. 3 is a schematic diagram of obtaining a mandible motion direction in each TMJ image. In FIG. 3, a center between two temporal bone corners is a reference point. There is a mandible corner below the two temporal bone corners. A motion direction vector is obtained based on motion of the mandible corner between different frames.

At this point, the mandible motion direction in each TMJ image is obtained.

S004: Obtain a real mandible edge contour in each TMJ image based on an edge contour on which the mandible corners are located and the mandible motion direction in each TMJ image.

It should be noted that after the mandible motion direction in each TMJ image is determined, it can be determined that the edge of the mandible also has the same motion direction. In addition, because the edge of the mandible does not deform, artifacts occur at the edge in the TMJ image, resulting in a plurality of edges. The edge may be shortened due to the artifacts, but an overall shape of the edge is still fixed. Because the condyle of the mandible usually appears as a rounded projection, a curvature can be used to represent a shape of the condyle of the mandible. Therefore, a real mandible edge in a plurality of adjacent TMJ images can be determined based on the mandible motion direction and mandible edge similarity between adjacent TMJ images.

It should be noted that because the edge cannot be directly used to determine the motion direction, and the edge is round, a circumcircle of the edge is obtained, and a change direction of a center of the circumcircle is determined as a change direction of the edge.

The edge contour on which the mandible corners are located in each TMJ image is recorded as a mandible edge contour.

A vector of a center of a minimum circumcircle of each mandible edge contour in each TMJ image is obtained in a manner of obtaining the vector of the $z^{th}$ suspected mandible corner in the $i^{th}$ TMJ image.

In each TMJ image, the vector of the center of the minimum circumcircle of each mandible edge contour is recorded as a motion vector of each mandible edge contour.

The $i^{th}$ to $(i+t)^{th}$ TMJ images are recorded as reference TMJ images corresponding to the $i^{th}$ TJM image.

A direction of a sum vector of the motion vectors of all mandible edge contours in all reference TMJ images is recorded as a mandible edge contour motion direction corresponding to the $i^{th}$ TMJ image.

The similar mandibular edge index of the $i^{th}$ TMJ image is calculated based on the following formula:

$$P_i = \theta_i' \times \sum_{s=2}^{M} |a_s - a_{s-1}|$$

$P_i$ represents the similar mandibular edge index of the $i^{th}$ TMJ image. $\theta_i'$ represents a minimum included angle between the mandible motion direction and the mandible edge contour motion direction corresponding to the $i^{th}$ TMJ image. $a_s$ represents an average curvature of all mandible edge contours in the $s^{th}$ reference TMJ image. $a_{s-1}$ represents an average curvature of all mandible edge contours in the $(s-1)^{th}$ reference TMJ image. | | represents the absolute value function. M represents a quantity of the reference TMJ images.

It should be noted that $\theta_i'$ represents the minimum included angle between the mandible motion direction and the mandible edge contour motion direction corresponding to the $i^{th}$ TMJ, indicating that the motion directions are consistent. $|a_s - a_{s-1}|$ represents a difference between the average curvatures of all mandible edge contours in adjacent reference TMJ images. A larger difference indicates that the motion directions are more inconsistent.

A similar mandibular edge index of each TMJ image is obtained through the foregoing method.

All TMJ images are equally grouped into a plurality of TMJ image sequences. The mandible edge contour in the TMJ image corresponding to the smallest similar mandibular edge index in each TMJ image sequence is used as the real mandible edge contour in each TMJ image.

It should be noted that a preset value is 5. An example in which a quantity of TMJ images in each TMJ image sequence obtained after equal grouping is the preset value is used for description.

At this point, all real mandible edge contours in the TMJ images are obtained.

S005: Construct a TMJ anatomical model based on the real mandible edge contours and the temporal bone edge contours in all TMJ images.

Three-dimensional reconstruction is performed through an AI algorithm based on the real mandible edge contours and the temporal bone edge contours in all TMJ images to generate the anatomical model of the TMJ.

The AI algorithm is a well-known technique, and a specific method is not described herein.

It should be noted that a real mandible edge in the TMJ image is determined. Edge position changes of the mandible and the temporal bone are tracked and recorded by analyzing a video sequence during mouth opening and closing. Tracked edge position change data is visualized. A dynamic change diagram of the TMJ during mouth opening and closing is established. The three-dimensional anatomical model of the TMJ is constructed by extracting information from image data.

It should be noted that based on the anatomical model and the dynamic change diagram, a doctor can evaluate a functional status of the joint and identify any anomaly or pathological change, such as articular disc displacement or osteoarthritis. For a patient who needs surgery, the TMJ model can be used to simulate surgery, predict surgical results, and plan key surgical steps, such as incision position determining and prosthesis placement.

The embodiments of the present disclosure further provide a system for simulating TMJ surgery based on an AI technology, including a memory, a processor, and a computer program stored in the memory and executable on the processor. The processor, when executing the computer program, implements S001 to S005.

At this point, this embodiment is completed.

The foregoing descriptions are merely preferred embodiments of the present disclosure, and not intended to limit the present disclosure. Any modifications, equivalent replacements, improvements, and the like made within the principle of the present disclosure shall all fall within the protection scope of the present disclosure.

What is claimed is:

1. A method for simulating temporomandibular joint (TMJ) surgery based on an artificial intelligence (AI) technology, comprising the following steps:
   obtaining a plurality of TMJ images and corners corresponding to each corner in each TMJ image in other TMJ images;
   constructing a coordinate system of each TMJ image; in the coordinate system, obtaining a motion synchronization degree of any two corners in each TMJ image based on a distance between coordinates of each of the any two corners in the TMJ image and coordinates of the corresponding corner in an adjacent TMJ image; and obtaining temporal bone corners and a temporal bone edge contour in each TMJ image based on the motion synchronization degree of and a distance between the any two corners in each TMJ image;
   obtaining a plurality of mandible corners and a mandible motion direction based on a distance between the temporal bone corners in each TMJ image and coordinates of the corners in the TMJ image in the coordinate system;
   obtaining a real mandible edge contour in each TMJ image based on an edge contour on which the mandible corners are located and the mandible motion direction in each TMJ image; and
   constructing a TMJ anatomical model based on real mandible edge contours and temporal bone edge contours in all TMJ images;
   wherein the step of obtaining the motion synchronization degree of the any two corners in each TMJ image based on the distance between the coordinates of each of the any two corners in the TMJ image and the coordinates of the corresponding corner in the adjacent TMJ image is implemented based on the following formula:

$$B_{u,v} = \frac{1}{n-1} \sum_{i=1}^{n-1} \left( \frac{|C_{u,i} - C_{v,i}|}{C_{u,i} \times C_{v,i}} \right)$$

wherein $B_{u,v}$ represents a motion synchronization degree of a $u^{th}$ corner and a $v^{th}$ corner in each TMJ image; n represents a quantity of the TMJ images; $C_{u,i}$ represents a distance between coordinates of the $u^{th}$ corner in an $i^{th}$ TMJ image and coordinates of a corresponding corner in an $(i+1)^{th}$ TMJ image in the coordinate system; $C_{v,i}$ represents a distance between coordinates of the $v^{th}$ corner in the $i^{th}$ TMJ image and coordinates of a corresponding corner in the $(i+1)^{th}$ TMJ image in the coordinate system; and | | represents an absolute value function;

the step of obtaining the temporal bone corners and the temporal bone edge contour in each TMJ image based on the motion synchronization degree of and the distance between the any two corners in each TMJ image comprises the following steps:
obtaining a motion synchronization index between the any two corners in each TMJ image based on the motion synchronization degree of and the distance between the any two corners in each TMJ image; and
obtaining the temporal bone corners and the temporal bone edge contour in each TMJ image based on the motion synchronization index between the any two corners in each TMJ image;
the step of obtaining the motion synchronization index between the any two corners in each TMJ image based on the motion synchronization degree of and the distance between the any two corners in each TMJ image is implemented based on the following formula:

$$E_{u,v} = B_{u,v} \times \frac{1}{n} \sum_{i=1}^{n} |L_{i,u,v} - \overline{L}|$$

wherein $E_{u,v}$ represents a motion synchronization index between the $u^{th}$ corner and the $v^{th}$ corner in each TMJ image; $B_{u,v}$ represents the motion synchronization degree of the $u^{th}$ corner and the $v^{th}$ corner in each TMJ image; n represents the quantity of the TMJ images; $L_{i,u,v}$ represents an Euclidean distance between the $u^{th}$ corner and the $v^{th}$ corner in the $i^{th}$ TMJ image; $\overline{L}$ represents an average Euclidean distance between the $u^{th}$ corner and the $v^{th}$ corner in all TMJ images; and | | represents the absolute value function;
the step of obtaining the temporal bone corners and the temporal bone edge contour in each TMJ image based on the motion synchronization index between the any two corners in each TMJ image comprises the following step:
in each TMJ image, recording the two corners corresponding to a minimum motion synchronization index as the temporal bone corners, and an edge contour on which the temporal bone corners are located as the temporal bone edge contour;
the step of obtaining the plurality of mandible corners and the mandible motion direction based on the distance between the temporal bone corners in each TMJ image and the coordinates of the corners in the TMJ image in the coordinate system comprises the following steps:
in each TMJ image, recording a center point of a line segment connecting two temporal bone corners as a reference point, performing clockwise rotation from a horizontal right direction to a horizontal left direction to construct a semicircle with the reference point as a circle center and y times a distance between the two temporal bone corners as a radius, and recording corners in the semicircle which are not temporal bone corners as suspected mandible corners, wherein y represents a preset coefficient;
in the coordinate system, forming a vector of a $z^{th}$ suspected mandible corner in the $i^{th}$ TMJ image based on a distance and a direction from coordinates of the $z^{th}$ suspected mandible corner in the $i^{th}$ TMJ image to coordinates of a corresponding corner in the $(i+t)^{th}$ TMJ image;
performing anomaly detection on all suspected mandible corners through a local outlier factor (LOF) algorithm based on a direction of a vector of each suspected mandible corner in the $i^{th}$ TMJ image, to obtain abnormal mandible corners; and recording all suspected mandible corners except the abnormal mandible corners as the mandible corners; and recording a direction of a sum vector of the vectors of all mandible corners in the $i^{th}$ TMJ image as the mandible motion direction in the $i^{th}$ TMJ image;

the step of obtaining the real mandible edge contour in each TMJ image based on the edge contour on which the mandible corners are located and the mandible motion direction in each TMJ image comprises the following steps:

obtaining a similar mandibular edge index of each TMJ image based on the edge contour on which the mandible corners are located and the mandible motion direction in each TMJ image; and obtaining the real mandible edge contour in each TMJ image based on the similar mandibular edge index of each TMJ image;

the step of obtaining the similar mandibular edge index of each TMJ image based on the edge contour on which the mandible corners are located and the mandible motion direction in each TMJ image comprises the following steps:

recording the edge contour on which the mandible corners are located in each TMJ image as a mandible edge contour;

obtaining a vector of a center of a minimum circumcircle of each mandible edge contour in each TMJ image in a manner of obtaining the vector of the $z^{th}$ suspected mandible corner in the $i^{th}$ TMJ image;

in each TMJ image, recording the vector of the center of the minimum circumcircle of each mandible edge contour as a motion vector of each mandible edge contour;

recording the $i^{th}$ to $(i+t)^{th}$ TMJ images as reference TMJ images corresponding to the $i^{th}$ TJM image;

recording a direction of a sum vector of the motion vectors of all mandible edge contours in all reference TMJ images as a mandible edge contour motion direction corresponding to the $i^{th}$ TMJ image; and calculating a similar mandibular edge index of the $i^{th}$ TMJ image based on the following formula:

$$P_i = \theta'_i \times \sum_{s=2}^{M} |a_s - a_{s-1}|$$

wherein $P_i$ represents the similar mandibular edge index of the $i^{th}$ TMJ image; $\theta'_i$ represents a minimum included angle between the mandible motion direction and the mandible edge contour motion direction corresponding to the $i^{th}$ TMJ image; as represents an average curvature of all mandible edge contours in an $s^{th}$ reference TMJ image; $a_{s-1}$ represents an average curvature of all mandible edge contours in an $(s-1)^{th}$ reference TMJ image; | | represents the absolute value function; and M represents a quantity of the reference TMJ images; and the step of obtaining the real mandible edge contour in each TMJ image based on the similar mandibular edge index of each TMJ image comprises the following step:

equally grouping all TMJ images into a plurality of TMJ image sequences, and using the mandible edge contour in the TMJ image corresponding to a smallest similar mandibular edge index in each TMJ image sequence as the real mandible edge contour in each TMJ image.

2. A system for simulating TMJ surgery based on an AI technology, comprising a memory, a processor, and a computer program stored in the memory and executable on the processor, wherein the computer program, when executed by the processor, implements the steps of the method for simulating the TMJ surgery based on the AI technology according to claim 1.

* * * * *